United States Patent
Gustavsson

(10) Patent No.: US 9,884,167 B2
(45) Date of Patent: Feb. 6, 2018

(54) CATHETER WITH PARTIALLY SLITTED INSERTION AID

(71) Applicant: DENTSPLY IH AB, Molndal (SE)

(72) Inventor: Evelina Gustavsson, Onsala (SE)

(73) Assignee: DENTSPLY IH AB, Mölndal (SE)

( * ) Notice: Subject to any disclaimer, the term of this patent is extended or adjusted under 35 U.S.C. 154(b) by 0 days.

(21) Appl. No.: 14/601,273

(22) Filed: Jan. 21, 2015

(65) Prior Publication Data

US 2015/0141966 A1    May 21, 2015

Related U.S. Application Data

(63) Continuation of application No. 13/767,100, filed on Feb. 14, 2013, now abandoned.
(Continued)

(30) Foreign Application Priority Data

Mar. 5, 2012 (EP) .................................. 12158070

(51) Int. Cl.
*A61M 25/00* (2006.01)
*A61M 25/01* (2006.01)
*A61M 25/08* (2006.01)

(52) U.S. Cl.
CPC ...... *A61M 25/0102* (2013.01); *A61M 25/002* (2013.01); *A61M 25/013* (2013.01); *A61M 25/0111* (2013.01); *A61M 25/0017* (2013.01)

(58) Field of Classification Search
CPC ............ A61M 25/0102; A61M 25/002; A61M 25/0111; A61M 25/013; A61M 25/0017;
(Continued)

(56) References Cited

U.S. PATENT DOCUMENTS 3,470,604 A  10/1969  Zenick
3,613,684 A * 10/1971  Sheridan ................ A61B 17/34
                                                  128/207.29
(Continued)

FOREIGN PATENT DOCUMENTS

CH       414067     5/1966
CN       1281198    10/2006
(Continued)

OTHER PUBLICATIONS

European Searsh Report, Application No. 12158070.8, Published Aug. 16, 2012.
(Continued)

*Primary Examiner* — Adam Marcetich
(74) *Attorney, Agent, or Firm* — Perkins Coie LLP

(57) ABSTRACT

A tubular insertion aid for catheter manipulation is disclosed. The insertion aid is particularly suited for urinary catheters, such as hydrophilic urinary catheters for intermittent use. The insertion aid comprises a forward opening, a rearward opening and a slit opening extending along a part of the sidewall of the tubular insertion aid, so that a first portion of the tubular insertion aid in the axial direction forms a solid circumference around the tubular insertion aid, and a second portion in the axial direction is provided with the slit opening extending in an axial direction of the tubular insertion aid. The tubular insertion aid further comprises a first inward protrusion formed on the interior side of the tubular insertion aid in a part of the second portion being provided with the slit, wherein the first inward protrusion is arranged along a first protrusion line extending along the inward circumference of the tubular insertion aid essentially perpendicularly to the axial direction of the tubular insertion aid.

18 Claims, 5 Drawing Sheets

Related U.S. Application Data

(60) Provisional application No. 61/606,587, filed on Mar. 5, 2012.

(58) Field of Classification Search
CPC .............. A61M 25/0637; A61M 25/01; A61M 25/0662; A61M 25/02; A61M 25/09041; A61B 17/3415; A61F 2/0095; B25G 1/00; B25G 1/005; B25G 1/02; B25G 1/025; B25G 1/063; B25G 3/38
See application file for complete search history.

(56) References Cited

U.S. PATENT DOCUMENTS

| | | | | |
|---|---|---|---|---|
| 4,468,146 | A * | 8/1984 | Tabachnik | B43K 23/016 401/116 |
| 4,643,389 | A * | 2/1987 | Elson | A61M 39/284 24/543 |
| 4,735,618 | A * | 4/1988 | Hagen | A61M 5/3275 604/110 |
| 4,840,619 | A * | 6/1989 | Hughes | A61M 5/3271 604/187 |
| 4,846,808 | A * | 7/1989 | Haber | A61B 5/150389 600/576 |
| 4,921,479 | A | 5/1990 | Grayzel | |
| 5,069,669 | A * | 12/1991 | Kole | A61M 5/3275 604/192 |
| 5,084,032 | A * | 1/1992 | Kornberg | A61M 39/14 604/192 |
| 5,125,904 | A | 6/1992 | Lee | |
| 5,219,339 | A * | 6/1993 | Saito | A61M 25/0637 604/177 |
| 5,242,428 | A * | 9/1993 | Palestrant | A61M 25/01 604/265 |
| 5,279,581 | A * | 1/1994 | Firth | A61B 5/411 604/198 |
| 5,295,972 | A * | 3/1994 | Mischenko | A61M 5/3275 604/192 |
| 5,330,438 | A * | 7/1994 | Gollobin | A61M 25/0637 604/110 |
| 5,368,575 | A | 11/1994 | Chang | |
| 5,398,947 | A * | 3/1995 | Cook | B23B 31/202 279/133 |
| 5,441,504 | A | 8/1995 | Pohndorf et al. | |
| 5,800,399 | A * | 9/1998 | Bogert | A61M 25/0014 604/164.11 |
| 5,827,239 | A | 10/1998 | Dillon et al. | |
| 6,149,332 | A * | 11/2000 | Huang | B43K 23/10 401/88 |
| 6,299,589 | B1 | 10/2001 | Utterberg | |
| 6,554,807 | B2 | 4/2003 | Gollobin | |
| 6,613,014 | B1 | 9/2003 | Chi | |
| 7,476,223 | B2 | 1/2009 | McBride | |
| 2002/0002872 | A1* | 1/2002 | Wessel | B62K 23/04 74/502.2 |
| 2004/0020335 | A1* | 2/2004 | Chen | B25B 23/0035 81/438 |
| 2004/0068844 | A1* | 4/2004 | Lumpkin | B62K 21/26 16/421 |
| 2004/0186445 | A1* | 9/2004 | Raulerson | A61M 39/284 604/250 |
| 2004/0186447 | A1* | 9/2004 | Mori | A61M 25/0637 604/263 |
| 2005/0015076 | A1 | 1/2005 | Giebmeyer et al. | |
| 2005/0015934 | A1* | 1/2005 | Hu | B25G 1/00 16/430 |
| 2005/0267487 | A1 | 12/2005 | Christensen et al. | |
| 2006/0236522 | A1* | 10/2006 | Lin | B21D 53/70 29/527.2 |
| 2007/0066963 | A1 | 3/2007 | Tanghoj | |
| 2007/0239118 | A1* | 10/2007 | Ono | A61M 25/0631 604/263 |
| 2008/0027414 | A1 | 1/2008 | Tanghoj et al. | |
| 2008/0097362 | A1* | 4/2008 | Mosler | A61M 25/00 604/349 |
| 2009/0139380 | A1* | 6/2009 | Pyatt | B25G 1/102 81/489 |
| 2009/0208368 | A1 | 8/2009 | Waldrep et al. | |
| 2010/0241083 | A1 | 9/2010 | Fisher et al. | |
| 2010/0286664 | A1 | 11/2010 | Haslinger | |
| 2011/0060317 | A1* | 3/2011 | Frojd | A61M 25/0009 604/544 |
| 2011/0114520 | A1* | 5/2011 | Matthison-Hansen | A61M 25/002 206/364 |
| 2011/0123253 | A1* | 5/2011 | Matsui | A46B 5/04 401/269 |
| 2011/0162490 | A1* | 7/2011 | Chang | B25B 15/008 81/177.1 |
| 2011/0301551 | A1* | 12/2011 | Koehler | A61M 5/1626 604/263 |
| 2012/0073086 | A1* | 3/2012 | Rarick | B62K 21/26 16/436 |
| 2012/0239070 | A1* | 9/2012 | Wijay | A61B 17/320016 606/185 |
| 2013/0038579 | A1* | 2/2013 | Boyd | B43K 7/02 345/179 |
| 2014/0066905 | A1* | 3/2014 | Young | A61M 25/0113 604/544 |

FOREIGN PATENT DOCUMENTS

| | | |
|---|---|---|
| CN | 102481434 | 5/2012 |
| EP | 1504870 A2 | 2/2005 |
| EP | 1131022 | 8/2005 |
| EP | 1131022 B1 | 8/2005 |
| EP | 2106821 A1 | 10/2009 |
| EP | 2292294 A1 | 3/2011 |
| GB | 322426 | 12/1929 |
| SU | 1165412 | 7/1985 |
| WO | 200030575 | 6/2000 |
| WO | 2000030575 | 6/2000 |
| WO | 2000040284 | 7/2000 |
| WO | 2001017599 A1 | 3/2001 |
| WO | 2004089454 | 10/2004 |
| WO | 2011026929 | 3/2011 |

OTHER PUBLICATIONS

Russian Office Action issued for Application No. 2014115867, dated Jan. 24, 2017 (13 pages).
European Search Report, Application No. 10197422.8-1526, Published Jun. 14, 2011.
Chinese Office Action for Chinese Patent Application No. 201180062415.6, dated May 26, 2015, with translation (18 pages).
Chinese Office Action for Chinese Patent Application No. 201180062415.6, dated Sep. 30, 2015, with translation (12 pages).

* cited by examiner

CATHETER WITH PARTIALLY SLITTED INSERTION AID

RELATED DOCUMENTS

This application claims the benefit of priority of U.S. non-provisional application Ser. No. 13/767,100, filed Feb. 14, 2013, which claims the benefit of priority of U.S. provisional application Ser. No. 61/606,587, filed Mar. 5, 2012 and European application Serial Number 12158070.8, filed Mar. 5, 2012, which are herein incorporated by reference for all purposes.

TECHNICAL FIELD OF THE INVENTION

The present invention is related to a catheter, and in particular a urinary catheter, with an insertion aid to facilitate handling of the catheter.

BACKGROUND

Catheters, such as urinary catheters, and in particular catheters having hydrophilic coatings, are relatively difficult to handle, since the surface before application is very slippery. Further, direct contact with the insertable part of the catheter should preferably be avoided, in order to avoid contamination of the catheter, and thereby minimize the risk of e.g. urinary tract infections. Still further, many users of intermittent urinary catheterization are disabled or have poor dexterity for other reasons, and consequently, there is also for this ground a need for means for making manipulation and insertion of catheters easier and cleaner/safer.

To overcome these problems, many alternative insertion aids have been proposed during the last years. For example, EP 1 131 022 discloses an applicator which is formed as an integrated and detachable hose member arranged in the catheter package in which the catheter is arranged. However, as a consequence, the catheter package becomes relatively complicated and costly, and also, the operation of using this catheter assembly is relatively cumbersome.

Further, EP 2 106 821 discloses a catheter assembly in which an insertion aid is arranged as a tubular part arranged over the connector part of the catheter. Upon use, the tubular insertion aid may be loosened from its position on the connector, and moved along the catheter shaft. However, this solution is also relatively complicated and costly, since assembly of the product is quite complicated, and adequate connection of the tubular part on the connector and at the same time easy detachment by the user is difficult to achieve.

There is therefore still a need for a catheter assembly having an insertion aid which is easier to use and/or easier and more cost-efficient to produce.

SUMMARY OF THE INVENTION

There is therefore an object of the present invention to provide a catheter and a method of manufacture that at least partly overcome the above-discussed problems of the prior art.

This object is achieved by means of a catheter and a method for manufacture according to the enclosed claims.

According to a first aspect of the invention there is provided a tubular insertion aid for catheter manipulation, comprising a forward opening, a rearward opening and a slit opening extending along a part of the sidewall of the tubular insertion aid, so that a first portion of the tubular insertion aid in the axial direction forms a solid circumference around the tubular insertion aid, and a second portion in the axial direction is provided with the slit opening extending in an axial direction of the tubular insertion aid, the tubular insertion aid further comprising a first inward protrusion formed on the interior side of the tubular insertion aid in a part of the second portion being provided with said slit, said first inward protrusion being arranged along a first protrusion line extending along the inward circumference of the tubular insertion aid essentially perpendicularly to the axial direction of the tubular insertion aid.

The insertion aid may be used for catheter manipulation, thereby avoiding the need to directly touch the catheter, and in particular the insertable part of the catheter. This reduces the risk of contaminating the insertable part of the catheter prior to insertion. It may also be used to manipulate the catheter during and after withdrawal, thereby avoiding the risk of the user being contaminated by the used catheter.

The insertion aid hereby comprises a protrusion which may be engaged with a recession or the like in the catheter and/or catheter connector, thereby securely connecting the insertion aid to the catheter. The connection is a mechanical interlocking, which maintains the insertion aid in an intended stored position. At the same time, the insertion aid is easy to assemble on the catheter, and easy to disassemble before an intended use. This is due to the provision of the slit opening in the same axial section of the tubular insertion aid as the protrusion, so that the protrusion line and the slit opening intersect each other. Hereby, the slit opening provides an increased flexibility to the insertion aid in the vicinity of the protrusion, which facilitates assembling and disassembling. For example, the user may squeeze the first part of the tubular insertion aid, which forces slit opening to be further opened, and thereby the mechanical connection between the protrusion and the catheter to be loosened.

The new insertion aid also lends itself well for efficient manufacturing and assembly. The insertion aid in itself may e.g. be injection molded. Further, the simple and efficient connection between the insertion aid and the catheter ensures that the insertion aid remains in place on the catheter before use, and an intentional detachment. This also makes packaging of the catheter and the insertion aid easier. Thus, the insertion aid hereby remain safely in place during packaging, sterilization, transportation, storage, activation prior to use, during withdrawal from the catheter from the package, etc.—i.e. in all handling up to a deliberate detachment of the insertion aid. At the same time, detachment is made very simple, even for users with reduced dexterity.

After withdrawal of the insertion aid from the catheter the insertion aid is usable as an insertion aid for maneuvering the catheter during insertion into the human cavity.

Further, the insertion aid will always be kept securely in place before it is removed and used as an insertion aid. At the same time, if the user does not need an insertion aid for manipulation of the catheter, the insertion aid can be allowed to remain in its non-released state during the entire use. Even in this way of using the catheter, where the insertion aid remains non-detached, the insertion aid is to advantage, since it hereby provides an enlarged gripping portion for the catheter, which makes insertion and withdrawal of the catheter easier, especially for users with reduced dexterity.

The insertion aid is further easy to remove, and thereafter to move along the length of the elongate shaft, thereby facilitating contamination free handling of the catheter, which reduces the risk of urinary tract infections and the like.

In addition, the tubular insertion aid is easy and cost-efficient to produce, e.g. by injection molding, and also is easy to mount on the catheter during manufacturing, both manually and automatically.

The slit opening may extend entirely in the axial direction of the tubular insertion aid, or alternatively it may extend partly in the axial direction, and partly in other directions.

The tubular insertion aid may comprise only the first and second portions, in which case the forward opening is arranged in the first portion and the rearward opening arranged at the second portion. Preferably, the first portion is arranged between the second portion and the forward opening, and the second portion is preferably arranged between the first portion and the rearward opening. However, in addition, further portion of the tubular insertion aid in the axial direction may be provided, between the forward opening and the first portion, between the first portion and the second portion, and/or between the second portion and the rearward opening.

The solid circumference around the tubular insertion aid does not necessitate a uniform thickness around the circumference. However, it does imply an unbroken material connection around the circumference.

The first inward protrusion may comprise a solid protruding line, extending along the first protrusion line. However, the first inward protrusion may also comprise two or more protrusions arranged around said first protrusion line.

Further, the tubular insertion aid preferably comprises a second inward protrusion formed on the interior side of the tubular insertion, the second inward protrusion being arranged along a second protrusion line extending along the inward circumference of the tubular insertion aid essentially perpendicularly to the axial direction of the tubular insertion aid, wherein the second protrusion line is separated from the first protrusion line in the axial direction of the tubular insertion aid. Such a second or further protrusion may contribute further to the mechanical interlocking between the catheter and the tubular insertion aid. Preferably, the second protrusion is arranged to function as a stop, to prevent further advancement of the tubular insertion aid onto the connector of the catheter during assembly. Too far advancement may result in a too strong connection between the tubular insertion aid and the catheter, which would make subsequent detachment of the tubular insertion aid more difficult. Thus, the second protrusion makes manufacturing and assembly simpler and more cost-efficient, and also ensures that the insertion aid is easy to detach for the user. To this end, it is further preferred that the second protrusion line is arranged at or adjacent to the junction between the first and second portions of the tubular insertion aid. Hereby, the stopping function of the second portion essentially becomes unaffected by squeezing of the first portion of the tubular insertion aid. However, it may still, by the use of a somewhat greater force, be possible to advance the insertion aid further up over the connector of the catheter. This may be to advantage since it makes it possible to expose the entire shaft of the catheter, for users who need to make use of the entire length of the catheter.

Further, the design of the insertion aid, together with a possible relative softness and flexibility of the material of which the insertion aid is made, ensures that the catheter, and in particular hydrophilic coatings and the like, are not damaged, or at least that such damages are minimized.

In a preferred embodiment, the second portion of the tubular insertion aid extends between the first portion of the tubular insertion aid and the rearward opening of the tubular insertion aid, and the slit opening of the second portion does not extend all the way up to the rearward opening, thereby forming a solid circumference around the tubular insertion aid in the vicinity of the rearward opening. Hereby, the slit opening becomes a closed opening, being closed both in a forward and rearward end. This ensures that the increased flexibility afforded by the slit opening is only provided at an intermediate part of the tubular insertion aid, and both ends of the tubular insertion aid being unaffected by this increased flexibility. This provides an increased stability to the insertion aid, and an even better connection between the catheter and the insertion aid. Further, this is an advantage during manufacturing, since it hinders tubular insertion aids to be stuck together. Preferably, the solid circumference around the tubular insertion aid in the vicinity of the rearward opening is provided with a reduced wall thickness in the extension of the slit opening than in the rest of the circumference. Hereby, the closing of the rearward end of the slit opening functions as a rubber band, and is provided with increased elasticity and flexibility. However, a uniform wall thickness in the solid circumference in the vicinity of the rearward opening is also feasible.

Further, the tubular insertion aid is preferably at least partly funnel shaped. In a preferred embodiment, the first portion of the insertion aid is at least partly funnel shaped, whereas the second portion has an essentially uniform diameter. It is also preferred that the rearward opening has a greater cross-sectional dimension than the forward opening.

The first portion may be provided with gripping means on the outwardly facing side. This makes gripping and squeezing of the first portion easier, which facilitates detachment of the tubular insertion aid from the catheter, and the use of the insertion aid for maneuvering the catheter. The gripping means may be formed by at least one of outward protrusions, corrugations, embossment and perforations.

The tubular insertion aid is preferably made of a flexible plastics material. The material may be any thermoplastic and/or thermosetting plastic materials which are usable for providing sufficient strength and flexibility for the intended use. In one embodiment, the tubular insertion aid may be made of thermoplastic elastomer, such as the commercially available Dryflex®.

According to a further aspect of the present invention, there is provided a catheter set comprising a catheter and the tubular insertion aid of the above-discussed type, and wherein the catheter comprises a forward insertion part and a rearward connector part, wherein the connector part forms a waist having a cross-sectional dimension of lower extension than the surrounding portions of the connector part, and wherein, in a storage position, the insertion aid is arranged around the connector part of the catheter so that the first protrusion line of the tubular insertion aid overlies said waist of the catheter, thereby detachably connecting the tubular insertion aid to the catheter. By means of this aspect of the invention, similar advantages and possible additional features as discussed above in relation to the first aspect of the invention are obtainable.

By "connector" and "connector part" is in this application meant the rearward end of the catheter, which may be used to connect the catheter to external tubing, a urine collection bag, or the like. However, notably the connector need not necessarily be connected to anything, but may also in itself serve as a discharge end. Further, the connector may have a specific geometrical shape, such as being at least partly funnel shaped, having a frusto-conical shape, being flared, or the like. However, in the most general sense, the connector need not have a geometrical shape distinguishing it from the catheter tube, and may e.g. in its simplest form be the integrated rearward part of the catheter tube. Further, the connector may be a separate component, which is connected to the catheter tube during manufacturing, or may be formed as an unified, integral part of the catheter tube.

The connector part of the catheter preferably comprises a discharge end which forms an inwardly funnel shaped end. The outwardly surface of the connector end may have an essentially uniform diameter, or be funnel shaped as well.

Preferably, the connector part of the catheter and the tubular insertion aid are both made of the same material. This facilitates manufacturing, and also provides an adequate friction between the connector and the tubular insertion aid. Further, the elongate shaft and the tip portion of the catheter may also be of the same material. Alternatively, the various components of the catheter may be of different materials. For example, the connector part and the insertion aid may be formed by two different materials. Other parts of the catheter, such as the tip portion, may optionally also be formed by a different material than the rest of the elongate shaft.

The catheter is preferably a hydrophilic catheter, wherein the forward insertion part is at least partly provided with a hydrophilic material exhibiting low-friction surface properties when wetted. The hydrophilic material is preferably arranged at least on an insertable length of the catheter.

Further, the catheter is preferably a urinary catheter, and preferably a urinary catheter for intermittent use.

According to still another aspect of the present invention, there is provided a catheter assembly comprising a catheter set of the above-discussed type, and a package enclosing said catheter set. By means of this aspect of the invention, similar advantages and possible additional features as discussed above in relation to the first aspect of the invention are obtainable.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION OF PREFERRED EMBODIMENTS

Figure 1:
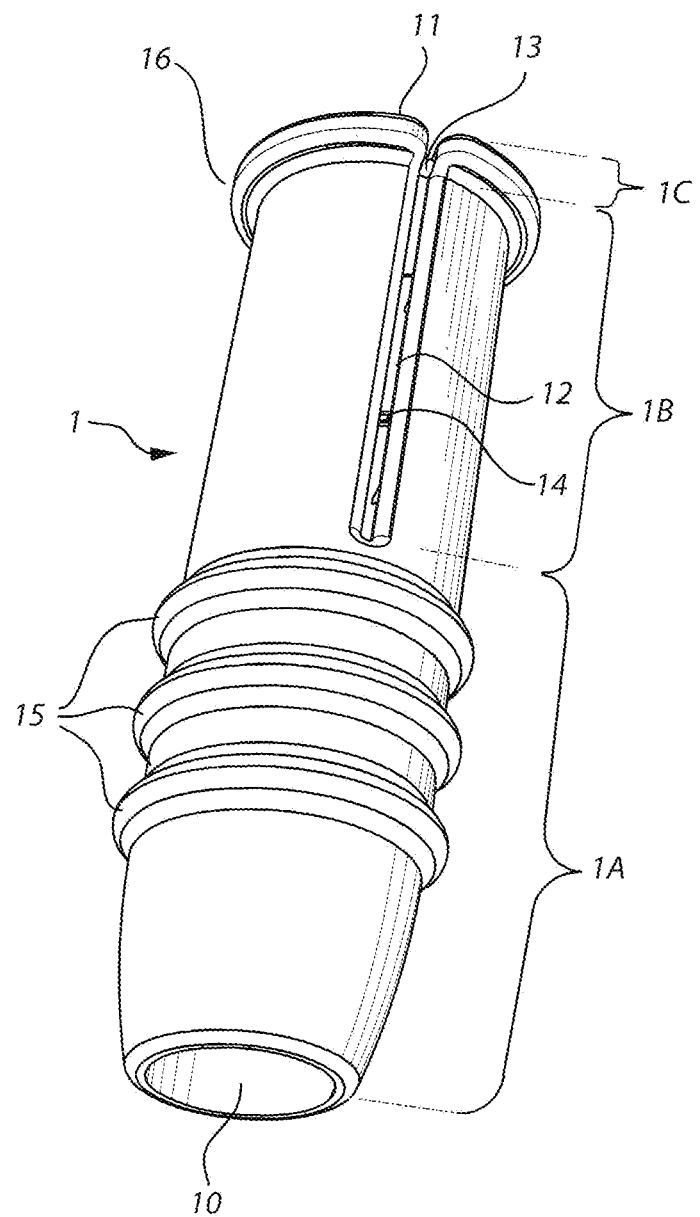
FIG. 1 is a side view in perspective of a tubular insertion aid according to an embodiment of the present invention.

In the following detailed description, preferred embodiments of the present invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention.

The following discussion is in particular concerned with hydrophilic urinary catheters for intermittent use. However, the invention can also be used in relation to other types of urinary catheters, or other types of catheters in general.

Figure 2:
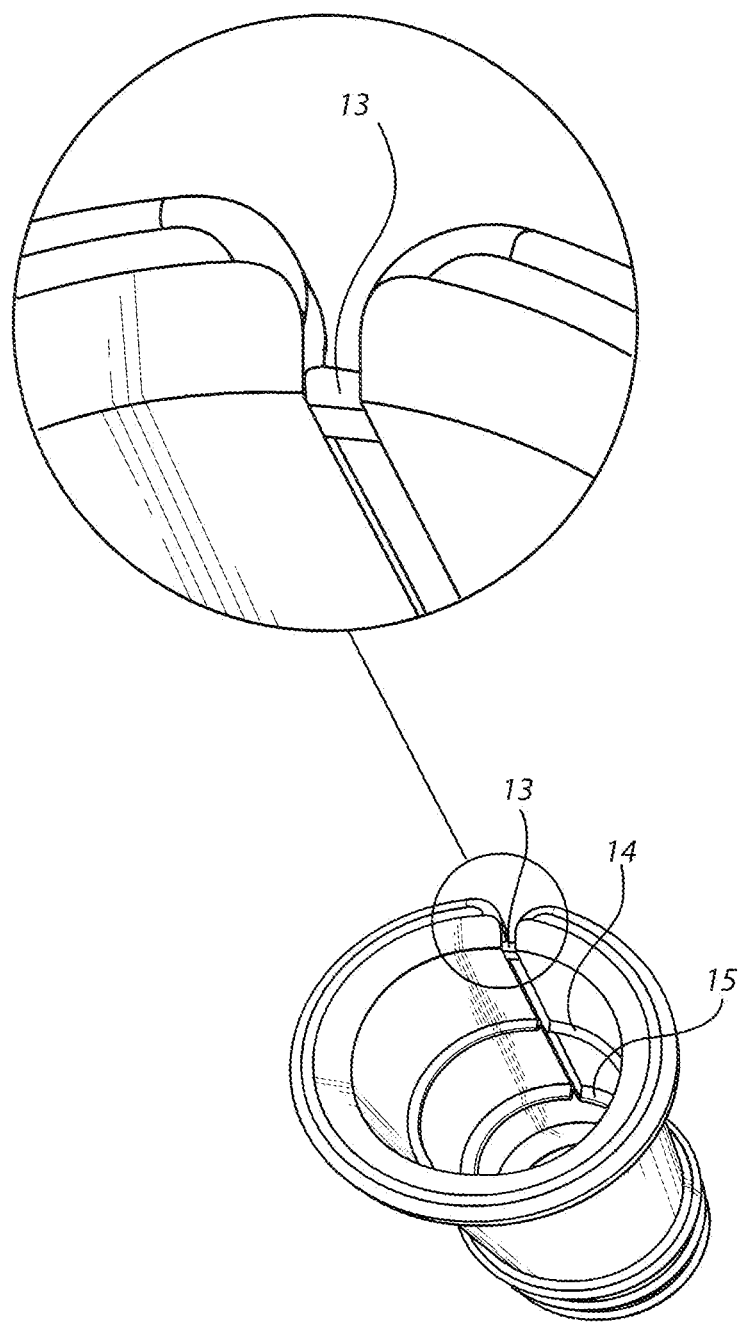
FIG. 2 is an elevated view in perspective of the tubular insertion aid of FIG. 1.

A tubular insertion aid according to an exemplary embodiment will first be discussed with reference to FIGS. 1 and 2. The tubular insertion aid is preferably intended to be arranged over the rearward part or connector part of the catheter in a storage position, and to be loosened and moved along the catheter during insertion of the catheter, for contamination free manipulation of the catheter.

The tubular insertion aid 1 comprises a generally tubular member, comprising a forward opening 10, a rearward opening 11 and a slit opening 12 extending along a part of the sidewall of the tubular insertion aid. Hereby, the tubular insertion aid comprises a first portion 1A of the tubular insertion aid in the axial direction which forms a solid circumference around the tubular insertion aid, and a second portion 1B in the axial direction is provided with the slit opening extending in an axial direction of the tubular insertion aid. In assembled condition on a catheter, the forward opening 10 is facing the insertion end of the catheter, whereas the rearward opening 11 is facing the rearward, non-insertable end of the catheter.

The slit opening 12 may extend entirely in the axial direction of the tubular insertion aid, as in the shown exemplary embodiment. However, alternatively it may extend partly in the axial direction, and partly in other directions, i.e. in an oblique direction in relation to the axial direction.

The tubular insertion aid may comprise only the first portion 1A and second portion 1B, in which case the forward opening 10 is arranged in the first portion 1A and the rearward opening 11 is arranged in the second portion 1B. However, further portions may be provided between the forward opening and the first portion, between the first and second portions, and/or between the second portion and the rearward opening.

In the exemplary embodiment, the first portion 1A is arranged between the second portion 1B and the forward opening 10, and the second portion is arranged between the first portion 1A and a third portion 1C. The third portion is arranged between the second portion 1B and the rearward opening 11. Similar to the first portion, the third portion 1C forms a solid circumference around the insertion aid. However, whereas the first portion 1A extends over a substantial part of the tubular insertion aid, the third portion 1C has a very short axial extension. Preferably, the first portion extends over 10-60% of the axial length of the tubular insertion aid, and more preferably over 25-50%. The second portion preferably extends over 20-70% of the axial length of the tubular insertion aid, and more preferably over 30-60%. The third portion preferably extends over 0-10% of the axial length of the axial length of the tubular insertion aid, and preferably over 1-5%. Hereby, the slit opening becomes a closed opening, being closed both in a forward and rearward end. This ensures that the increased flexibility afforded by the slit opening is only provided at an intermediate part of the tubular insertion aid, and both ends of the tubular insertion aid being unaffected by this increased flexibility.

In a preferred embodiment, the third portion presents a narrower thickness in the extension of the slit opening, whereby a narrow and thin cord 13 extends over the slit opening in the vicinity of the rearward end 11. This thin cord 13 hereby provides greater flexibility than the rest of the sidewalk forming the tubular insertion aid.

Further, the tubular insertion aid is preferably at least partly funnel shaped. In a preferred embodiment, the first portion 1A of the insertion aid is at least partly funnel shaped, whereas the second portion 1B, and the optional third portion 1C, have essentially uniform diameters. It is also preferred that the rearward opening 11 has a greater cross-sectional dimension than the forward opening 11.

The tubular insertion aid further comprises a first inward protrusion 14 formed on the interior side of the tubular insertion aid in a part of the second portion 1B being provided with the slit opening 12. The first inward protrusion 14 is arranged along a first protrusion line extending along the inward circumference of the tubular insertion aid essentially perpendicularly to the axial direction of the tubular insertion aid. This first protrusion may be engaged with a recession or the like in the catheter, thereby securely connecting the insertion aid to the catheter, as will be discussed further below. The first inward protrusion 14 may comprise a solid protruding line, extending along the first protrusion line. However, the first inward protrusion may also comprise two or more protrusions arranged around said first protrusion line.

Further, the tubular insertion aid preferably comprises a second inward protrusion 15 formed on the interior side of the tubular insertion, the second inward protrusion being arranged along a second protrusion line extending along the inward circumference of the tubular insertion aid essentially perpendicularly to the axial direction of the tubular insertion aid. This second protrusion line is separated from the first protrusion line in the axial direction of the tubular insertion aid. Preferably, the second protrusion 15 is arranged at or adjacent to the juncture between the first portion 1A and the second portion 1B. It is further preferred that the second protrusion 15 is formed directly forward of the slit opening 12. In such a position, the second protrusion may function as a stop, to prevent too far advancement of the tubular insertion aid onto the connector during assembly. However, other locations of the second protrusion are also feasible, and it is also possible to have third or further protrusion, arranged along third or further protrusion lines. Such additional protrusions may serve to provide increased mechanical interlocking on the catheter, or to serve as abutments to prohibit unwanted advancement.

The first portion 1A may further be provided with gripping means on the outwardly facing side. This makes gripping and squeezing of the first portion easier, which facilitates detachment of the tubular insertion aid from the catheter, and the use of the insertion aid for maneuvering the catheter. The gripping means may be formed by at least one of outward protrusions, corrugations, embossment and perforations. In the shown example, gripping means 15 in the form of outwardly protruding gripping lines are provided. In the illustrative example, three gripping lines are provided. However, fewer or more gripping lines may also be used, and other types of gripping means are also feasible.

Further, an outwardly protruding gripping line or flange 16 is preferably also arranged in the vicinity of the rearward opening.

The tubular insertion aid is preferably made of a flexible plastics material. The material may be any thermoplastic and/or thermosetting plastic materials which are usable for providing sufficient strength and flexibility for the intended use. In one embodiment, the tubular insertion aid may be made of thermoplastic elastomer, such as the commercially available Dryflex®. However, other materials are also feasible. For example, the material may be one or several of: a polymer material, such as polyurethanes, thermoplastic rubbers, polyvinylchloride, other vinyl polymers, polyesters, polyether block amid, polypropene, polyethen polyamide and styren-ethen/butadiene-styren co-polymer, polyacrylates and polysiloxanes. The material may also be a polymer blend comprising a polyolefin and a composition having molecules with active hydrogen groups, and preferably a composition having molecules with active hydrogen groups. The polyolefin can comprise at least one polymer selected from the group: polyethene, polypropene, and styrene block copolymer (SEWS). The composition having molecules with active hydrogen groups can be a polymer having active hydrogen groups bound to the polymer via nitrogen, such as polyamide or polyurethane.

The insertion aid is preferably sufficiently flexible to be compressed, e.g. by applying a pressure between the thumb and the index finger, over the elongate shaft. Sufficient flexibility of the insertion aid may be accomplished by forming it by a sufficiently flexible material, and/or by having a sufficiently narrow thickness. Further, the thickness may vary over the tubular part, thereby making some parts more flexible than others. Preferably, the tubular part has a Shore A hardness in the range 40-80, and preferably in the range 50-70, and most preferably in the range 55-65 . . . .

In a preferred embodiment, the Shore A hardness is above 40, and most preferably above 50. In another preferred embodiment, the Shore A hardness is preferably below 80, and even more preferably below 70. In another preferred embodiment, the Shore A hardness is about 60.

The tubular insertion aid can e.g., be manufactured by injection molding.

The tubular insertion aid as discussed above is preferably assembled on a rearward end of a catheter, and a catheter set comprising a catheter and a tubular insertion aid now be discussed with reference to FIGS. 3A and 3B.

The catheter 2 comprises a forward insertion part 20 and a rearward connector part 21, wherein the connector part forms a waist 22 having a cross-sectional dimension of lower extension than the surrounding portions of the connector part 21. In a preferred embodiment, the connector part 21 comprises a funnel shaped rearward end 21A, tapering in a direction towards the insertion end of the catheter, and a somewhat enlarged forward end 21B. The forward end 21B is preferably not funnel shaped. The forward end 21B may further be provided with corrugations or the like, to enhance the gripping and connecting properties. However, other configurations of the rearward connector part 21 are also feasible, such as a cylindrical outer surface being provided with an indentation or similar waist, or other types of a non-circular circumference.

The forward insertion part 20 preferably comprises an elongate shaft with an insertion end. The insertion end is preferably provided with one or several drainage openings, in fluid communication with an internal lumen of the catheter.

The rearward connector part 21 further comprises a discharge end, and is preferably arranged with an inwardly tapering inner surface, arranged to be connectable to a frusto-conical connection to external tubing or a urine collection bag.

The catheter may be of any size suitable for catheterization. For use by female users the elongate shaft preferably has a length in the range of 5-20 cm, such as in the size of 15 cm. For male users, the elongate shaft preferably has a length in the range 18-45 cm, such as in the size of 40 cm.

In order to further facilitate insertion of the catheter, the elongate shaft may comprise a hydrophilic material at the surface, said hydrophilic material providing a low-friction character to the catheter surface when wetted. For example, the elongate shaft can be made essentially entirely of a hydrophilic material. Alternatively, the elongate shaft may be provided with a hydrophilic surface coating.

The hydrophilic material may e.g. be polyvinyl pyrrolidone (PVP), but many other types of hydrophilic coatings are known in the art, and may be used in the context of the present invention. The hydrophilic coating provides a low-friction character to the catheter when wetted, thereby facilitating insertion of the catheter into the urethra, and reducing the risk of pain etc.

More specifically, the hydrophilic material may comprise material(s) selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethyl-vinyl ether and maleinic acid anyhydride. The preferred hydrophilic polymer is polyvinylpyrrolidone.

In case the hydrophilic material is arranged as a coating, the coating preferably forms a polyurea network, whereby said polyurea network forms a covalent bond to said active hydrogen groups in the substrate. Alternatively, the hydrophilic coating may form an ester bond or an epoxy bond to said active hydrogen groups in the substrate.

The coating may also comprise an osmolality-increasing compound, as is e.g. taught in EP 0 217 771.

In an assembled storage position, the tubular insertion aid, as discussed thoroughly above, is arranged over the connector part of the catheter so that the first protrusion line of the tubular insertion aid overlies said waist of the catheter, thereby detachably connecting the tubular insertion aid to the catheter. Such a storage position is illustrated in FIG. 3A.

The connection is a mechanical interlocking, which maintains the insertion aid in an intended stored position. At the same time, the insertion aid is easy to assemble on the catheter, and easy to disassemble before an intended use. This is due to the provision of the slit opening in the same axial section of the tubular insertion aid as the protrusion, so that the protrusion line and the slit opening intersect each other. Hereby, the slit opening provides an increased flexibility to the insertion aid in the vicinity of the protrusion, which facilitates assembling and disassembling. For example, the user may squeeze the first part 1A of the tubular insertion aid, which forces slit opening to be further opened, and thereby the mechanical connection between the protrusion and the catheter to be loosened.

Figures 3A, 3B:
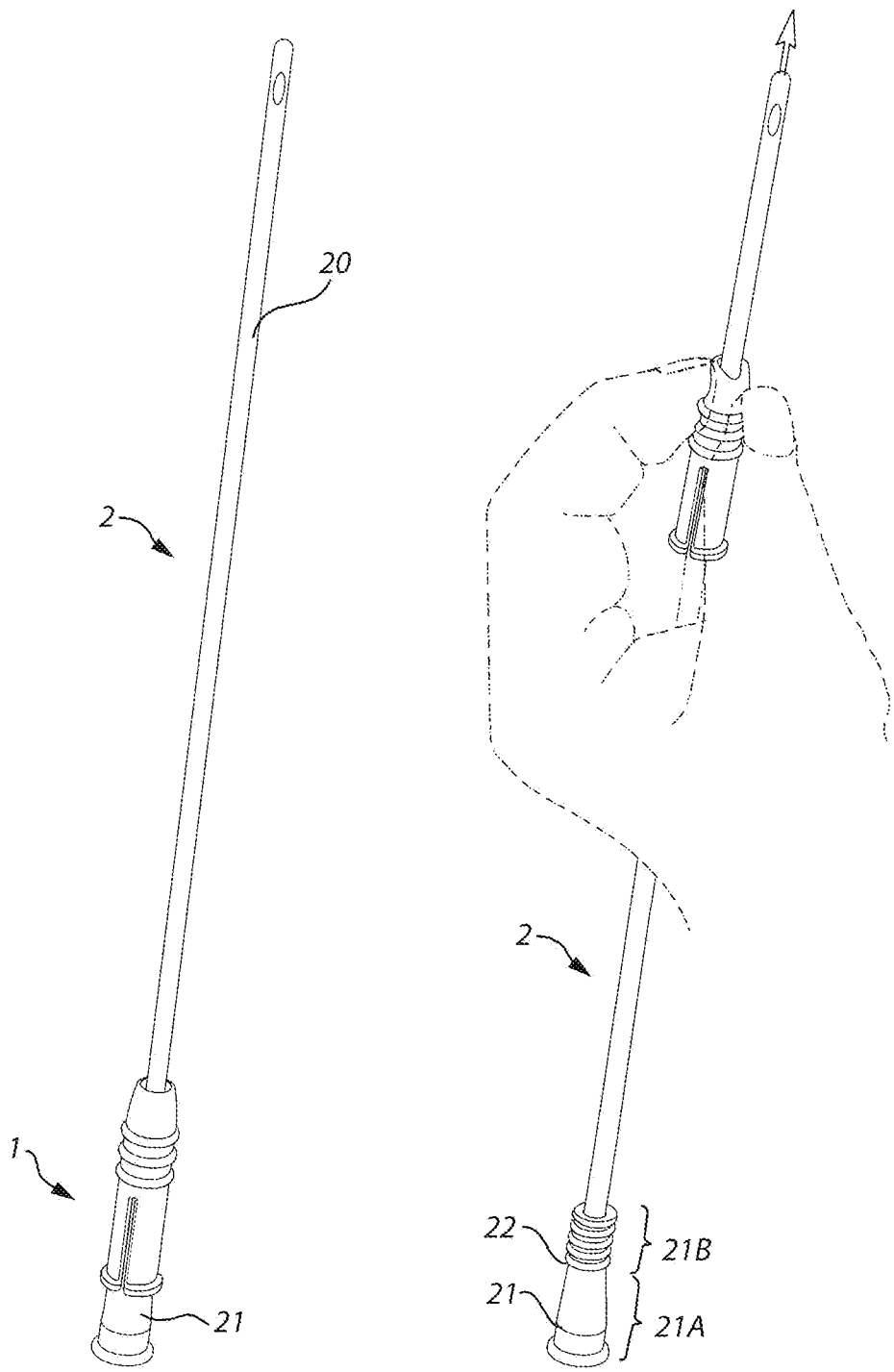
FIGS. 3A and 3B are perspective side views of catheters having tubular insertion aids, illustrated in a storage and use position, respectively.

After withdrawal of the insertion aid from the catheter the insertion aid is usable as an insertion aid for maneuvering the catheter during insertion into the human cavity, as is illustrated in FIG. 3B. In this position, the insertion aid may be move along the length of the elongate shaft, thereby facilitating contamination free handling of the catheter, which reduces the risk of urinary tract infections and the like.

The connector part of the catheter and the tubular insertion aid are preferably both made of the same material. This facilitates manufacturing, and also provides an adequate friction between the connector and the tubular insertion aid. Further, the elongate shaft and the tip portion of the catheter may also be of the same material. Alternatively, the various components of the catheter may be of different materials.

Figure 4:
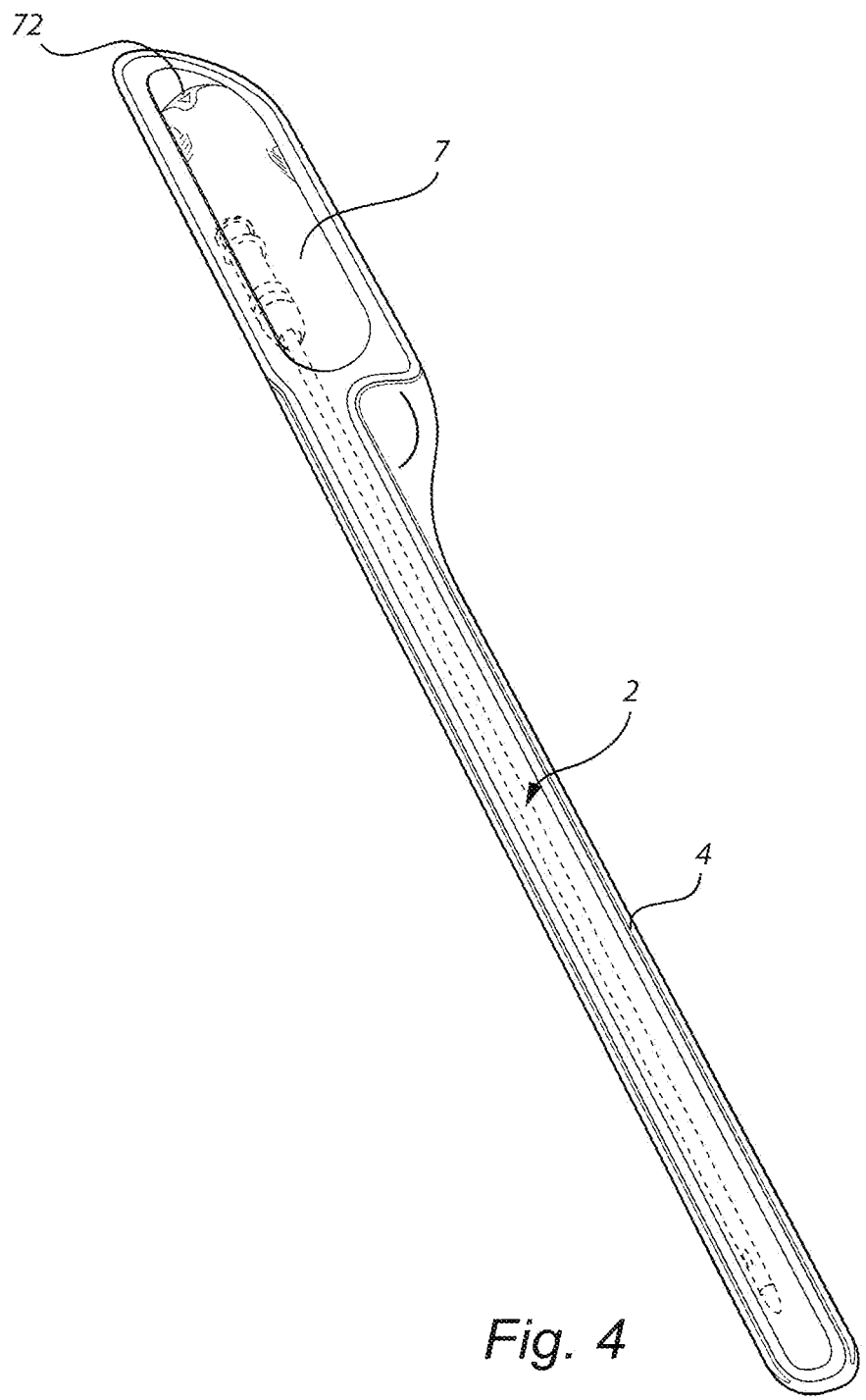
FIG. 4 illustrates a catheter assembly including a tubular insertion aid.
Figure 5:
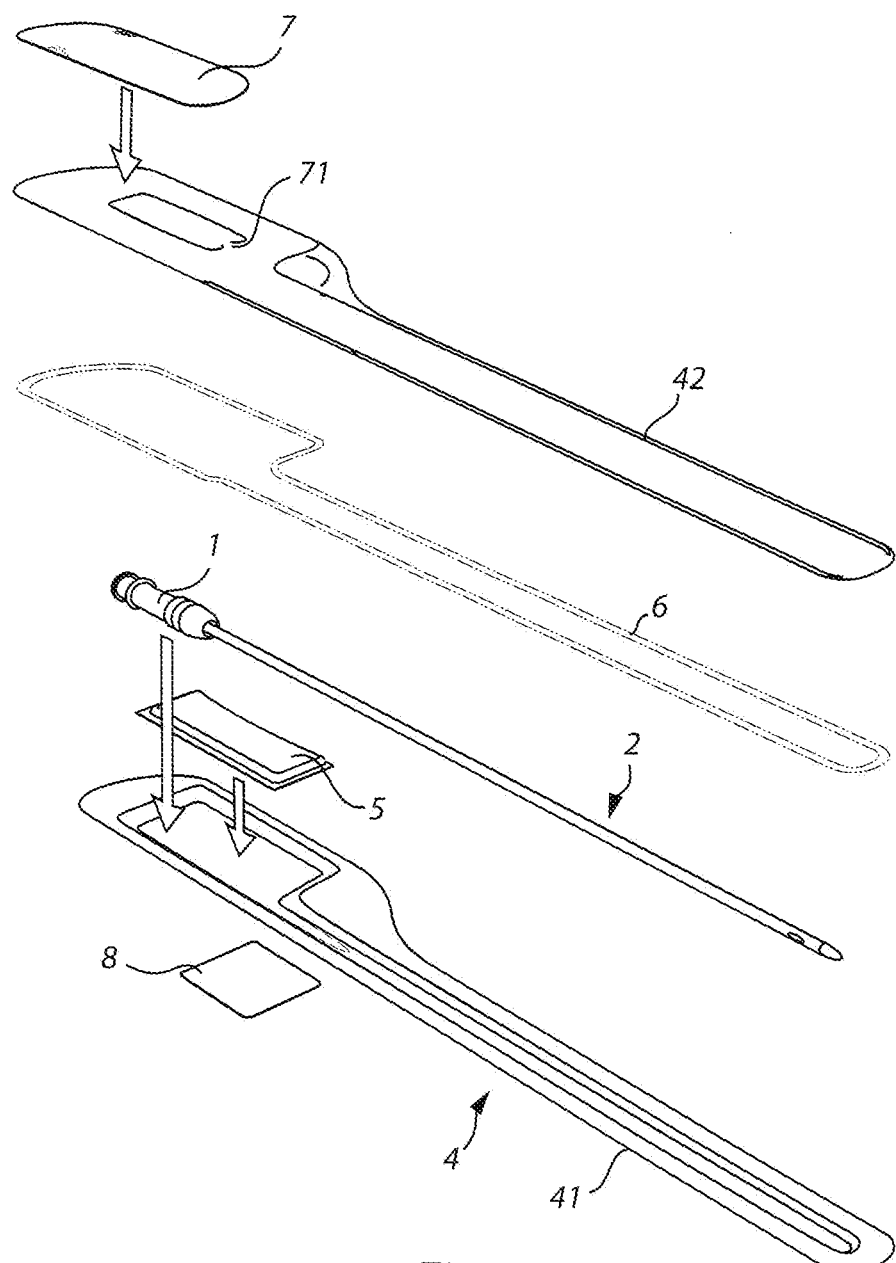
FIG. 5 illustrates an exploded view of the catheter assembly of FIG. 4.

The above-discussed catheter set, comprising a catheter and a tubular insertion aid, may be arranged in a catheter assembly comprising a catheter set of the above-discussed type, and a package 4 enclosing said catheter set. Such a catheter assembly will now be disclosed with reference to FIGS. 4 and 5.

The package 4 encloses a catheter 2, and a thereon assembled tubular insertion aid 1, as discussed previously. The package may further comprise a wetting fluid, preferably arranged in a wetting fluid container 5, for activation of the hydrophilic surface coating of the catheter.

The wetting fluid may be arranged separate from the catheter, in a wetting fluid container 5, such as a pouch or a sachet. The wetting fluid container is openable by means of e.g. exerting a pressure to the container, whereby the wetting fluid is released into the package, thereby wetting the hydrophilic surface of the catheter. However, alternatively the wetting fluid may be arranged in direct contact with the catheter and the hydrophilic surface during storage, thereby providing an immediately ready-to-use catheter assembly.

The wetting fluid is preferably an aqueous liquid, such as water or saline. Such wetting fluid containers and wetting fluids are per se well known in the art.

The package may be formed of sheet materials, such as a first sheet material 41 and a second sheet material 42, connected around the edges to form an inner cavity housing the catheter and the wetting fluid. The first and second sheet materials are preferably connected around the edges by means of welding, forming a welded edge joint 6. Preferably, the first and second sheet materials comprise laminated sheets, having a weldable inner layer and a protective outer layer. However, one or both of the sheets may alternatively be non-laminated, and be made of e.g. extruded or co-extruded material. The sheet materials are preferably of a flexible plastics material. For example, the sheets can be made of polymer materials such as polyethen, polypropylene, polyamide, and PET, or the receptacle can be made from a laminate of such polymer materials and/or aluminum, aluminum oxide, or oriented polypropylene (OPP).

One of the sheets may also be deep-drawn into a through shape.

Further, the package is operable, for withdrawal of the catheter prior to an intended use. To this end, the package may be provided with tear openings, peel openings, or the like. For example, the sheets may be arranged to be peelable apart from each other at one or several locations. However, preferably the opening is arranged as a resealable opening. Such a resealable opening may e.g. be formed by forming a wholly or partially cut through non-closed loop 71 in one of the sheets, and to add a further opening sheet 7 on top of this loop. Attachment of the sheet 7 may e.g. be made by adhesive.

In addition, there may be provided means for attaching the catheter package to a wall, a sink or the like. Such means may e.g. comprise an adhesive area arranged on one of the sheets, preferably the sheet not provided with the opening, and covered by a detachable cover sheet 8.

A method for producing a catheter assembly of this type includes the steps of:

Assembling a tubular insertion aid on a catheter.

Arranging the catheter and a wetting fluid container on one of the sheets. This sheet is preferably deep-drawn into a trough shape.

Connecting the second sheet on top of the first sheet, thereby closing the package.

Optionally, attaching the opening sheet and the cover sheet to the package.

Naturally, the order of these steps may be different, and e.g. the package may be partly closed prior to insertion of the catheter and/or the wetting fluid container. Further, attachment of the opening sheet and/or the cover sheet may be performed before or after any of the other steps.

The present invention has now been disclosed with reference to specific exemplary embodiments. However, it will be acknowledged by the skilled addressee that several modifications are possible. For example, the tubular insertion aid may be provided with further parts, further inner or outer protrusions, further slit openings, and the like. Further, the tubular insertion aid may be used for other types of catheters, e.g. catheters having differently designed connector ends, and the catheter set may also be arranged in many different forms of catheter assemblies.

The above-discussed and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements.

The invention claimed is:

1. A tubular insertion aid for catheter manipulation, comprising a forward opening, a rearward opening and a slit opening extending along a part of the sidewall of the tubular insertion aid, so that a first portion of the tubular insertion aid in the axial direction forms a solid circumference around the tubular insertion aid, and a second portion in the axial direction is provided with the slit opening extending in an axial direction of the tubular insertion aid, the tubular insertion aid further comprising a first inward protrusion formed on the interior side of the tubular insertion aid in a part of the second portion being provided with said slit, wherein the first inward protrusion is arranged along a first protrusion line extending along the inward circumference of the tubular insertion aid essentially perpendicularly to the axial direction of the tubular insertion aid, such that said slit opening provides an increased flexibility to the tubular insertion aid.

2. The tubular insertion aid of claim 1, further comprising a second inward protrusion formed on the interior side of the tubular insertion, the second inward protrusion being arranged along a second protrusion line extending along the inward circumference of the tubular insertion aid essentially perpendicularly to the axial direction of the tubular insertion aid, wherein the second protrusion line is separated from the first protrusion line in the axial direction of the tubular insertion aid.

3. The tubular insertion aid of claim 2, wherein the second protrusion line is arranged at or adjacent to the junction between the first and second portions of the tubular insertion aid.

4. The tubular insertion aid of claim 2, wherein said second inward protrusion is formed directly forward of said slit opening such that it functions as a stop to prevent further advancement of the tubular insertion aid.

5. The tubular insertion aid of claim 1, wherein the second portion of the tubular insertion aid extends between the first portion of the tubular insertion aid and the rearward opening of the tubular insertion aid, and wherein the slit opening of the second portion does not extend all the way up to the rearward opening, thereby forming a solid circumference around the tubular insertion aid in the vicinity of the rearward opening such that said increased flexibility is only provided at an intermediate part of said tubular insertion aid.

6. The tubular insertion aid of claim 5, wherein the solid circumference around the tubular insertion aid in the vicinity of the rearward opening is provided with a reduced wall thickness in the extension of the slit opening than in the rest of the circumference.

7. The tubular insertion aid of claim 1, wherein the tubular insertion aid is at least partly funnel shaped.

8. The tubular insertion aid of claim 1, wherein the rearward opening has a greater cross-sectional dimension than the forward opening.

9. The tubular insertion aid of claim 1, wherein the first portion is provided with gripping means on the outwardly facing side.

10. The tubular insertion aid of claim 9, wherein the gripping means is formed by at least one of outward protrusions, corrugations, embossment and perforations.

11. The tubular insertion aid of claim 1, wherein the tubular insertion aid is made of a flexible plastics material, such as any combinations of a thermoplastic material, a thermosetting plastic material or a thermoplastic elastomer material.

12. A catheter set comprising a catheter and the tubular insertion aid of claim 1, wherein the catheter comprises a forward insertion part and a rearward connector part, wherein the connector part forms a waist having a cross-sectional dimension of lower extension than the surrounding portions of the connector part, and wherein, in a storage position, the insertion aid is arranged around the connector part of the catheter so that the first protrusion line of the tubular insertion aid overlies said waist of the catheter, thereby detachably connecting the tubular insertion aid to the catheter.

13. The catheter set of claim 12, wherein the connector part of the catheter and the tubular insertion aid are both made of the same material.

14. The catheter set of claim 12, wherein the catheter is a hydrophilic catheter, wherein the forward insertion part is at least partly provided with a hydrophilic material exhibiting low-friction surface properties when wetted.

15. The catheter set of claim 12, wherein the catheter is a urinary catheter, and preferably a urinary catheter for intermittent use.

16. A catheter assembly comprising a catheter set of claim 12 and a package enclosing said catheter set.

17. The tubular insertion aid of claim 1, wherein said first protrusion line and said slit intersect each other.

18. The tubular insertion aid of claim 1, wherein said slit extends partly in said axial direction of said tubular insertion aid, and partly in other directions in relation to said axial direction.

* * * * *